United States Patent
Pushpangadan et al.

(10) Patent No.: US 7,172,772 B2
(45) Date of Patent: Feb. 6, 2007

(54) HERBAL COMPOSITION FOR GASTROINTESTINAL DISORDERS

(75) Inventors: Palpu Pushpangadan, Lucknow (IN); Chandana Venkateswara Rao, Lucknow (IN); Rawat Ajay Kumar Singh, Lucknow (IN); Shanta Mehrotra, Lucknow (IN); Sanjeev Kumar Ojha, Lucknow (IN); Amresh, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 18 days.

(21) Appl. No.: 10/812,201

(22) Filed: Mar. 29, 2004

(65) Prior Publication Data
US 2005/0142227 A1 Jun. 30, 2005

Related U.S. Application Data

(63) Continuation of application No. PCT/IN03/00406, filed on Dec. 29, 2003.

(51) Int. Cl.
*A61K 36/54* (2006.01)
(52) U.S. Cl. .......... 424/739; 424/725
(58) Field of Classification Search ............. None
See application file for complete search history.

(56) References Cited

U.S. PATENT DOCUMENTS

| 5,728,384 A | 3/1998 | Tokuyama |
| 6,187,313 B1 | 2/2001 | Segelman |
| 2003/0119916 A1 | 6/2003 | Fowler |

OTHER PUBLICATIONS

Heinrich, Phytotherapy Research (2000), vol. 14, pp. 479-488.*
Puri et al. Journal of Ethnopharmacology (2000), vol. 71, pp. 89-92.*
Singh et al. Journal of Ethnopharmacology (2002), vol. 81, pp. 31-41.*

* cited by examiner

*Primary Examiner*—Susan Hoffman
(74) *Attorney, Agent, or Firm*—Schwegman, Lundberg, Woessner & Kluth P.A.

(57) ABSTRACT

The invention provides a novel herbal antidiarrhoeal dosage form for the treatment of functional gastrointestinal disorders such as irritable bowel syndrome and diarrhea. The antidiarroheal herbal formulation comprises the decoction of *Cissampelos pareria, Mangifera indica, Cinnamomum* sp. and *Buchanania lanzan* with the conventional additives to form the oral dosage forms, which include syrup, tablets, capsules and powders ready for suspension.

37 Claims, No Drawings

HERBAL COMPOSITION FOR GASTROINTESTINAL DISORDERS

CROSS-REFERENCE TO RELATED PATENT APPLICATION

This application is a continuation of International Patent Application PCT/IN03/000406, with an international filing date of Dec. 29, 2003.

TECHNICAL FIELD

The present invention relates to the development of health protective herbal antidiarroeal composition.

BACKGROUND AND PRIOR ARTS

Diarrhoea is a condition, which results from the failure of one or more functions of alimentary canal. The alimentary canal receives mixes, digests and absorbs a wide variety and unpredictable amount of food with remarkable efficiency. What is left of the mixture of the food at the end of the alimentary canal is finally excreted as a small and convenient volume of the solid waste. Failure of the one or more of the aforementioned processes results in the passage of inconveniently bulky and liquid stools at increased frequency and is termed "Diarrhoea". Diarrhoea is also defined as the passage of loose, liquids or watery stools. Diarrhoea is caused due to any of the following causes: abnormal motility, disturbances in intestinal permeability, or the presence of osmotically active, nonabsorbable substances in the human gut. Broadly classified as acute and chronic diarrhoea. The acute diarrhoea (gastroenteritis) is mainly infectious; the pathological mechanism may be toxin production (preformed toxin, enterotoxin and cytotoxin), enteroadherence, mucosal-invasion (minimal, variable and severe) and systemic infection (viral hepatitis). The various other infectious agents may be classified as nonopportunistic pathogens (*Shigella, Salmonella, E. histolytica, Giardia lamblia* etc.), opportunistic infections (protozoa and viruses), human immunodeficiency virus (bacteria). Chronic diarrhoea may again be classified as inflammatory, osmotic, secretary, altered intestinal motility and factitious.

Despite tremendous development and achievements in science and medical science, several diseases are still challenging to human beings and efforts are on to conquer them. Even as we step into the new century with exciting prospect of gene therapy, herbal medicine remains one of the common forms of therapy available to world population. With the modern antidiarrhoeal agents not giving complete cure to the disease, there is a constant lookout for agents from the traditional system, which can provide complete cure to the disease, rather than treating the symptoms of the disease.

*CISSAMPELOS PAREIRA* (Linn.) Hirsuta

Family: Menispermaceae

Part used: Roots

Botanical description: *Cissampelos pareira* (Linn.) Hirsuta is a variable, lofty, slender, dioecious, perennial, sub erect or climbing herbs and shrubs, distributed in the tropical and subtropical world, ascending up to an altitude of 2,000 mtrs. Rootstock woody, perennial; leaves usually peltate or orbicular-reniform, ovate-sub-reniform, with a truncate-cordate base, glabrous or hairy above, 3–12 cm across; flowers greenish yellow, male in axillary, fascicled, pilose cymes or panicles, female in 6–15 cm long, pendulous racemes; drupes small, ovoid-sub-globose or obovoid, compressed, scarlet red, hirsute; seeds horse-shoe shaped. All parts of the plant are used as medicine. The dried roots form the drug, commonly known as FALSE PAREIRA BRAVA, and sometimes confused with the TRUE PAREIRA BRAVA, derived either from Chondrodendron tomentosum Ruiz and Pav., a native of Peru and Brazil, or *C. platyphyllum* Miers (Chopra et at, 1958). The drug consists of long, cylindrical, oval, or compressed pieces of the root, entire or longitudinally split, 0.1–1.20 cm×1.2–10.0 cm; bark grayish brown, longitudinally wrinkled, transversely crossed by annular elevations, interior wood yellowish gray, porous with concentric rings and medullary rays; aromatic and sweetish at first, turning intensely bitter later. Approximately 1.7 tones of root are cultivated every year in India (wealth of India, Vol. 3 (Revised), 1992, 591–593).

Medicinal use: Plant juice with jaggery and eggs is given internally for minor injuries. The poultice of leaves is applied to abscesses, sores, scabies, itches, pimples, boils and burns. The decoction, mixed with lemon and garlic juice and salt is given as stomachic. Being wound healer, antidote and kushthaghna, paste of leaves and root is used in fistula, purities, skin disorders and snake poison externally. Internally it is useful in anorexia, indigestion, abdominal pain, diarrhoea and dysentery. It is blood purifier and has anti-inflammatory property. It is also used in cough and dyspnoea and as it purifies breast milk it is used in various disorders of breast milk secretion. It is a potent diuretic.

Phytochemistry: The root and leaves contain several alkaloids and essential oil (0.2%). The methiodide and methchloride derivatives of hayatine (alkaloid) were reported to be potent neuromuscular blocking agents and produces varying degrees of fall in blood pressure (Patnaik et al, *Ind. J. Exp. Biol.* 11, 1973, 89–94). The methiodide was found to be one-third as potent as tubocurarine chloride and 1.5 times as potent as gallamine. Hayatine methocholride has a direct inotropic effect on the isolated cardiac muscle.

Pharmacology: The roots posses astringent, mild tonic, diuretic, stomachic, antilithic, analgesic, antipyretic and emmenagogue properties. They are frequently prescribed for cough, dyspepsia, dropsy, urino-genital troubles such as prolapsus uteri, cystitis, haemorrhage and menorrhagia, and calcular nephritis (Kirtikar and Basu, 1933, Vol. 3, 2146–2147). The juice is given to cattle also for curing diarrhoea. The root-paste is eruptions on the body of babies (Bhatnagar et al, *Ind. J. Med. Res.* 49, 1961, 799–807). Cissampareine, a bis-benzyl-isoquinoline alkaloid, showed a significant and reproducible inhibitory activity against human carcinoma cells of the naso-pharynx in cell culture. The roots show significant antibacterial activity against gram-positive organisms than against gram-negative strains (Adesina, *Fitoterapia.* 53, 1982, 147–162). An ethanolic extract (50%) of the stem and root shows CNS-depressant activity. The plant is also mentioned for the antidiarrhoeal properties ethnobotanically (Jain, 1991), but there was no scientific validation of the plant for this activity.

*MANGIFERA INDICA*

Family: Anacardiaceae

Part used: Seed Kernels

Botanical description: A large number of mango types, estimated at over 1000 are grown in various parts of India, each having its own peculiar taste, flavour and consistency of pulp. The trees dies not bear abundant fruit in the humid zones of lower Bengal, Assam, Kerala, and southeast Madras, since there is no chilly winter in these regions. The mango cannot stand frost and therefore does not thrive in the hills of Punjab, Uttar Pradesh and the temperate regions of Himachal Pradesh and Kashmir above 900 m. In the frost-free plains and hills of Peninsular India, the mango grows from sea level up to 1,200 m., but is commercially unsuccessful at elevations above 900 m. The mango is the most popular and the choicest fruit of India and occupies a prominent place among the best fruits of the world. Few other tropical fruits have the historic reputation mango possesses and few others are so intimately connected with Indian folklore. Mangoes thrive in parts of North India where temperature is as high as 115–120° F. Prevail during the summer; however, high temperature accompanied by strong wind breaks, preferably shisham (*Dalbergia sissoo*) and other trees, are planted to the south-west of mango plantations to arrest the winds. Young and unripe fruits are usually acidic and used in pickles, chutney, amchur and culinary preparations. Ripe fruits are preserved by canning or used in the manufacture of juice and squash, jams and jellies, preserves (murraba) and am papar.

Medicinal use: The bark is used in diphtheria and rheumatism. It is believed to possess a tonic action on the mucus membrane. Dried flowers are astringent and are used for diarrhoea, chronic dysentery and bleeding disorders. The dried kernel is used as feed for cattle and poultry.

Phytochemistry: Analysis of the flesh of Indian mangoes gave the following average values: green mango—moisture, 90.0; protein, 0.7; fat, 0.1; carbohydrates, 8.8; mineral matter, 0.4; calcium, 0.01; and phoshorus, 0.02%; iron, 4.5 mg/100 g; carotene (as vitamin A), 150 i.u., riboflavin, 30 μg; and ascorbic acid, 3 mg/100 g; ripe mango—moisture, 86.1; protein, 0.6; fat, 0.1; carbohydrates, 11.8; fibre, 1.1; mineral matter, 0.3 mg/100 g; carotene (as vitamin A), 4.800 i.u.; nicotinic acid, 0.3 mg; riboflavin, 50 μg; and ascorbic acid 13 mg/100 g. The sugar and acid contents vary widely with variety and stage of maturity 9Table 4). Table 5 gives pH, sugar and β-carotene conents of pulps of some vrieties of ripe mango (Hlth Bull., No. 23, 1951, 46; Cheema et al., Indian J. Agric. Sci., 1950, 20, 259).

The green tender fruit is rich in starch during ripening, the starch is hydrolysed into reducing sugars and a part of the latter is synthesized into sucrose. Unripe, fully developed mangoes of pickling varieties contain citric, malic, oxalic, succinic and two unidentified acids (probably di- or tri-basic acids); citric acid is the dominant constituent. As the fruit ripens, the acidity gradually decreases with a steep fall at the ripe stage. The amnio acids present in the non-protein nitrogen fraction of the mango fruit are: aspartic acid, glutamic acid, alanine, glycine, methionine, leucines and possibly cystine and γ-amino-butryic acid (Govindarajan & Sreenivasaya, Curr. Sci., 1950, 19, 234). The concentration of carotenoid pigments increases during ripening: the rate of increase of β-carotene is greater than that of others and an average-sized mango may synthesize as much as 1,200 μg of β-carotene in a day. The fruit is a rich source of potassium. Analysis of pulp ash (ash content, 0.53%) gave the following values: potassium ($K_2O$), 47.37; calcium (CaO), 6.38; magnesium (MgO), 1.62; Phosphorus ($P_2O_5$), 6.49; sulphur ($SO_3$), 3.67; and chlorine, 3.88%, Copper (1.9 μg/g) and iodine (16 μg/kg) are present in the ripe fruit.

Pharmacology: The extracts of leaves, bark, stem and unripe fruit exhibits moderate antibacterial activity against *Mcrocroccus pyogenes* var. *aureus*. The occurrence of anti-fungal properties has been reported. The seed kernels have an astringent taste. They are used as human food of certain parts of India in times of scarcity. They are some times roasted or boiled for eating (Wealth of India, 1992).

*CINNAMOMUM* Sps. (F. Hamilt.) Nees and Eberm.
Family: Lauraceae
Part used: Leaves and Barks
Botanical description: The species is the source of tejpat leaves used extensively in north India as a spice. The bark of the tree, known in trade as Indian cassia bark or Indian Cassia Lignea, is collected from trees growing at the foot of Sikkim and Himalayas. The plant is a medium sized tree, 7.5 m in height and 1.35 m in girth, distributed in tropical and subtropical Himalayas at an altitude of 1,000–1800 m, in Sikkim, Assam and Mizorum (Agarwal et al, *Indian Perfumer*. Vol. XXI, No. 1, 1977, 15–20). Leaves found cultivated in Tripura. Bark dark brown: leaves opposite or sometime alternate, elliptic to oblong-lanceolate, glabrous, 3-nerved at base, pink when young; flowers pale yellow, pubescent, in panicles; fruits black, ovoid, on the thickened peduncle and enlarge base of the perianth.

Medicinal use: The leaves are reported to be hypoglycemic, stimulant, carminative, antidote for scorpion sting and are used in colic, diarrhoea and rheumatism. They are considered hot and cardiac and are used with long pepper and honey in coughs and cold. Two teaspoonfuls of the powder given to diabetic patients four times a day for one month, accompanied by controlled diet, significantly reduces the blood sugar level and helps in release or manufacture of more insulin (Kirtikar & Basu, $2^{nd}$ ed., 1987, Vol. 1, 499–505).

The dried leaves act as antioxidant to oils and fats. The inner bark of the shoots of the cinnamon tree is a powerful local stimulant, which acts to ease the stomach and relieve spasms; it is also a mild astringent. The leaves are bitter, sweet, aromatic, thermogenic, alexeteric, anthelmintic, diuretic, stimulant, carminative and tonic. They are used in cardiac disorders, inflammations, helminthiasis, dyspepsia, strangury, colic, hyperptyalism, ophthalmia, vitiated conditions of vata, diarrhoea, proctitis, proctalgia, hepatopathy and splenopathy (Anonymous, 1994). Essential oil of the leaves has been reported for the antifungal activity against *Rhizocotnia bataticola, Fusarium moniliforme, Rhizoctonia solani, Pythium vexans* and *Alternaria helianthi* (Girjune et al, *Indian drugs*. 16, 1978, 24–26). The plant was active against *S. cerevesiae* at higher doses while inactive against *B. subtilis* and *E. coli* (Minakshi et al, *J. of Spices and Aromatic Crops*. 8(2), 1999, 135–144). The plant leaves oil is reported to active against *E. coli, P. aeruginosa, S. faecalis* and *S. pyogenes* (Current Sci, 1978, 47(13), July 5, 454–455). The essential oils of the leaves were potentially active (at 1000 ppm) against the *Trichophyton mentagrophytes* and *Microsporum audounil* causing ringworm diseases in animals and human being (Yadav and Dubey, *Ind. J. Pharm. Sci.* 6, 1994, 227–230). It has also found active for the cure of dermatomycosis in the form of the herbal formulation as active against *Trichophyton mentagrophytes* and *Microsporum audounil* (Yadav et al, *J. Med. Aromatic Plant Sci.* 1999, 347–351).

Phytochemistry: The leaves yield an essential oil (0.3–0.6%). A sample of oil from Kumaun hills (UP) and Joginder Nagar shows the following physicochemical characteristics, respectively: sp gr30*, 0.9730–0.9876, 0.9349; ester val, 54.13, 45.49; ester val after acetylation, 149.82, 152.70; aldehyde content, 49.5, 38.4 and phenol content in trace, 4.7–5.2% (Sood et al, 1979). The nD28=1.4791, d28=0.9034 and [α] D28=+6 (Nath et al, 1994). The chemical composition of two oils was as follows, respectively; cinnamic aldehyde, 41.2, 12.8; linalool, 15.7, 50.3; eugenol, 13.3, 1.0; eugenol acetate, 12.5,-; β-caryophyllene, 4.0,-; benzaldehyde, 4.1, 1.1; camphor, 3.2,-; cadinene, 3.1, -: and α-terpineol, 1.8, 2.9% (Iijas, 1978). Among the various components identified in the essential oil of Cinnamomum sps., linalool was reported as the main constituent and constituted 60.73% of the oil (Nath et al, J. of Spices and Aromatic Crops. 3(1), 1994, 33–35). A sample of oil from Assam (yield, 2%) has, however, been found to contain as high as 80–85 percent eugenol. The oil from the bark contains cinnamaldehyde (70–85%) as a major constituent. The leaves also contain 3,4',5,7-tetrahydroxy flavone, 3,3',4', 5,7-pentahydroxy flavone, kaempferol-3-O-glucopyranoside, kaempferol-3-O-sophoroside, kaempferol-3,7-di-O-rhamnopyranoside and quercetin 3-O-rutinoside.

Pharmacology: Drug powder when administered with diabetes (insulin independent) has shown decrease in glucose level when kept on sugar and starch free regulated diet (1800 calories/day) for one month (Tripathi et al, J. Res. Indian. Med. Yoga H. 19, 1979, 159–160; Chandola et al, J. Res. Ayur. Siddha. 1, 1980, 275–281). The Cinnamomum sps. Blume (Chinese name: Rougui, English name: Chinese cinnamon) is recommended in stomach ache; Diarrhoea, shock; cold; clammy extremities; cough and wheezing; pain in the lower part of the body and knees; dysmenorrhoea, amenorrhoea, low blood pressure; frostbite.

Buchanania lanzan linn
Family Anacardiaceae
Part used: Bark
Botanical Description: The genus includes 20 species of tree and shrubs, 6 of which occur in India. It is distributed in tropical Asia, Australia & the Pacific Islands. The tree is found in dry deciduous forest throughout India and Burma; in northwestern India from Sutluj to Nepal ascending to 3000'. The wood is light grey to greyish brown, some times with a light yellow cast, heartwood dark brown and rather lustrous while first exposed. The bark powder is buff to brown in color. It possesses slightly pungent odour and astringent taste.

Medicinal properties: The leaves are reported for their tonic and cardiotonic properties, their powder is common medicine for the wounds. The stem exudes a pale colour gum, which is used in intercostals pains. The gum dissolve in cow's milk is used internally in rheumatic pains.

Phytochemistry: Triglyceride composition of Buchanania lanzan seed oil were studied by Sengupta and Roychoudhury (J Sci Food Agric. 28(5), 2001, 463–468) and the flavonoids of the leaves were studied by Arya et al (J. Ind. Chem. Soc. 65, 1988, 882–883) while myricetin 3'-rhamnoside-3-galactoside was identified by Arya et al (Phytochemistry. 31 (7), 1992, 2569–2570). The presence of triterpenoids, saponins, reducing sugars and flavonoids is also reported. The bark contains 13.4% of tannins and 9.4% of non-tannins.

Pharmacology: A pellucid gum, resembling Bassora gum, exudes from wounds on stress. Effect of water extract of the bark of Buchanania lanzan linn. on behaviour and chromatophores of a fresh water fish, Labeo rohita was studied. (Chaudhary et al, J. Environ Biol. 22(3), 2001, 229–31). Products of plant given to mothers after childbirth or to invalids were studied for immunostimulant activity using the macrophage migration index (MMI) as a parameter of macrophage activation and cell-mediated immunity and haemagglutinating antibody (HA) titres and plaque-forming cell (PFC) counts as parameters of humoral immunity (Puri et al. J. Ethnopharmacol. 71(1–2), 2000, 89–92).

Hitherto, we present a novel synergistic herbal formulation, which contains plants, which have been used traditionally for the treatment of diarrhoea. Hence a study was undertaken to develop a synergistic combination of the traditionally used plants to develop a novel formulation effective in the treatment of diarrhoea.

OBJECTS OF THE INVENTION

The main object of the present invention to provide a novel antidiarrhoeal herbal formulation.

Another objective of the present invention is to that the plants used in the invention possess high antioxidant, hepatoprotective, digestive, choleretic, nervine relaxant and good immuno-enhancing properties.

Yet another object of the present invention is to prepare herbal formulation(s) with a combination of the plants which are used in diarrhea, intestinal discomforts.

SUMMARY OF THE INVENTION

Accordingly the present invention, a herbal formulation is useful in the treatment of diarrhea. The herbal formulation comprising Cissampelos paereia, Mangifera indica, Cinnamomum sps. and Buchanania lanzan which are used for high antioxidant, hepatoprotective, digestive, choleretic, nervine relaxant and good immuno-enhancing properties.

DETAILED DESCRIPTION OF THE INVENTION

Accordingly, the present invention provides a novel antidiarrhoeal herbal synergistic formulation useful for the treatment of acute ulcers of stomach and duodenum, said formulation comprising:

In an embodiment of the invention, synergistic pharmaceutical composition useful for the treatment of gastrointestinal disorders, said composition comprising extracts obtained from the plant Cissampelos pareira, Mangifera indica, Cinnamomum sp, Buchanania lanzan and optionally with pharmaceutically acceptable additives.

In still another embodiment of the invention, the said composition is useful for treating gastrointestinal disorder.

In still another embodiment of the invention, gastrointestinal disorder is diarrhea.

In yet another embodiment of the invention, gastrointestinal disorder is dysentery.

In another embodiment of the invention, gastrointestinal disorder is gastric ulcer.

In still another embodiment of the invention, gastrointestinal disorder is duodenal ulcer.

In yet another embodiment of the invention, gastrointestinal disorder is stomachache.

In yet another embodiment of the invention, gastrointestinal disorder is spasmodic.

In another embodiment of the invention, gastrointestinal disorder is irritable bowel syndrome.

In still another embodiment of the invention, gastrointestinal disorder is in the form of antispasmodic.

In yet another embodiment of the invention, the herbal composition immediately relieves the acidity of the stomach by neutralizing the excess acid.

In still another embodiment of the invention, the said composition is a synergistic mixture of plant extracts having high antioxidant, hepatoprotective, digestive, choleretic, nervine relaxant and immuno-enhancing properties.

Yet in another embodiment of the present invention, a herbal composition to treat gastro-intestinal disorders, said composition comprising 5–10% by wt. of extract from *Mangifera indica,* 5–10% by wt. of *Cissampelos pareira* and 5–10% by wt. of *Cinnamomum* sp. *Buchanania lanzan* 5–10% optionally along with other pharmacologically acceptable binders, diluents and lubricants.

Still another embodiment of the present invention, wherein the plant extracts are obtained: from plant parts selected from root, seed and aerial parts.

Yet in another embodiment of the present invention, wherein the extract of *Cissampelos pareira* is obtained from root.

Yet in another embodiment of the present invention, wherein the extract of *Mangifera indica* is obtained from seed kernel.

Still in another embodiment of the present invention, wherein the extract of *Cinnamomum* sp. is obtained from leaves and bark.

Yet in another embodiment of the present invention, wherein the extract of *Buchanania lanzan* is obtained from bark.

Still in another embodiment of the present invention, wherein the extracts of plants are 50% aqueous alcoholic extract.

In another embodiment of the present invention, wherein the said binder used in herbal composition is selected from a group comprising starch, starch paste, gum acacia and carboxy methyl cellulose.

Yet in another embodiment of the present invention, wherein the diluent used is lactose.

Still in another embodiment of the present invention, wherein the lubricants used are from starch and lactose.

In another embodiment of the present invention, wherein the 66.7% w/w sugar syrup is used as a vehicle.

Yet in another embodiment of the present invention, wherein the said composition comprises about 15–50% wt of the total formulation.

Still in another embodiment of the present invention, a method of preparing a herbal composition, wherein the said method comprising:
a) obtaining the part of medicinal plants from a group comprising leaves, bark, root and aerial parts;
b) drying the plant part of step (a);
c) powdering the dried plant material of step (b) to a coarse powder.
d) extracting the powdered dried plant material with at a temperature in the range of 25 to 35° C.;
e) extracting the plant material with the aqueous alcohol in the ratio of 1:8 to 1:15 for 4–7 days;
f) concentrating the obtained extract at under reduced pressure at a temperature in the range of 40–60° C., and
g) obtaining the extract by lyophilising the concentrated extract for complete removal of solvent.
h) mixing the extract of *Mangifera indica, Cissampelos pareira, Buchanania lanzan* and *Cinnamomum* sp 5–15% by wt., along with other pharmacologically acceptable binders, diluents and lubricants to prepare the composition.

Yet in another embodiment of the present invention, wherein the extraction is carried out by using 40–50% aqueous ethanol.

In another embodiment of the present invention, wherein said composition is applied as oral dosage selected from a group comprising syrup, tablet, capsule and powder.

Still in another embodiment of the present invention, wherein the applied dosage is 25 to 100 mg/kg in castor oil induced diarrhea, which gives a % protection of 16.92 to 76.69.

In another embodiment of the present invention, wherein the applied dosage is 25 to 100 mg/kg in on castor oil-stimulated gastrointestinal transit, which gives a % curative ratio of 43.19 to 66.70.

In another embodiment of the present invention, wherein the applied dosage is 25 to 100 mg/kg in castor oil induced fluid accumulation, wherein the fluid accumulation is reduced to 2.14±0.34 to 1.12±0.10.

In another embodiment of the present invention, wherein the applied dosage is 25 to 100 mg/kg in castor oil induced fluid accumulation, wherein the concentration of sodium is reduced to 151.6±9.6 to 105.4±06.9.

In another embodiment of the present invention, wherein the applied dosage is 25 to 100 mg/kg in castor oil induced fluid accumulation, wherein the concentration of potassium is reduced to 6.4±0.71 to 5.6±0.31.

Still in another embodiment of the present invention, wherein the applied dosage of 25 to 100 mg/kg in indomethacin induced acute gastric ulcers results in the protection percentage of 27.03 to 75.38% and significant increase in gastric wall mucus.

Yet in another embodiment of the present invention, wherein the applied dosage of 25 to 100 mg/kg in cysteamine induced duodenal ulcers shows 41.7 to 90.2 incidence (treated) when compared to 80% incidence of ulcers in control.

In another embodiment of the present invention, wherein the composition immediately relieves the acidity of the stomach by neutralizing the excess acid.

Still in another embodiment of the present invention the first step in the preparation of these formulations involves a process for making, the plant material suitable for formulating into a tablet, capsule and liquid dosage form. The specified portion of the plant is collected and dried under shade at room temperature (25–35° C.) for 72 hours or until the material gets dried. The material is then powdered into a fine powdered. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets. Extracts were added in proper ratio to prepare the Syrup. The Syrup was prepared according to Indian Pharmacopoeia 1966. The novelty lies in the fact that the components of the formulation when applied individually do not show any significant efficacy against gastro-intestinal disorder. Some of the components have never been used for the treatment of diarrhoea earlier. However, when all the components applied together as composition, it shows remarkable results in the management of gastro-intestinal problem. In some of the cases the composition serves a better role than the standard synthetic drug, more surprisingly, the composition does not have any side effect unlike the synthetic standard drug.

Brief Description of Tables

Table 1. Effect of formulation(s) on castor oil induced diarrhea in rats.

Table 2. Effect of formulation (F5) in castor oil induced fluid accumulation in rats.

Table 3. Effect formulation (F5) on castor oil-stimulated gastrointestinal transit in rats.

Table 4. Effect of formulation (F5) on indomethacin induced acute gastric ulcers in rats.

Table 5. Effect of Formulation (F5) and ranitidine on cysteamine induced duodenal ulcers in rats.

The invention is illustrated by the following examples wherein the following samples are given by the way of illustration of the present invention and should not be construed to limit the scope of the present invention.

EXAMPLES

Example-1

*Cissampelos pareira* was collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16 mesh screen. Talc is added to the dried granules and then they are punched in the tablet punching machine to form uniform tablets. Extracts were added in proper ratio to prepare the Syrup. The Syrup was prepared according to Indian Pharmacopoeia 1966. The formulation F1 given below is useful for the treatment of various gastrointestinal disorders.

| FORMULATION (F1) | |
|---|---|
| *Cissampelos pareira* | 15% |
| Sodium banzoate | 0.5% |
| Simple sugar syrup | Qs to make volume 100% |

Example-2

*Cissampelos pareira* and *Mangifera indica*. Were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets. Extracts were added in proper ratio to prepare the Syrup. The Syrup was prepared according to Indian Pharmacopoeia 1966. The formulation F2 is useful for the treatment of various gastrointestinal disorders.

| FORMULATION (F2) | |
|---|---|
| *Cissampelos pareira* | 15% |
| *Mangifera indica.* | 15% |
| Sodium banzoate | 0.5% |
| Simple sugar syrup/water | Qs to make volume 100% |

Example-3

*Cissampelos pareira*, *Mangifera indica* and *Cinnamomum* sps. Were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.0.15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets. Extracts were added in proper ratio to prepare the Syrup. The Syrup was prepared according to Indian Pharmacopoeia 1966. The formulation is useful for the treatment of various gastrointestinal disorders.

| FORMULATION (F3) | |
|---|---|
| *Cissampelos pareira* | 10% |
| *Mangifera indica* | 10% |
| *Cinnamomum* sps. | 10% |
| Sodium banzoate | 0.5% |
| Syrup containing sugar | Qs to make volume 100% |

Example-4

*Buchanania lanzan* linn. was collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form.15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets. Extracts were added in proper ratio to prepare the Syrup. The Syrup was prepared according to Indian Pharmacopoeia 1966. The formulation F4 is useful for the treatment of various gastrointestinal disorders.

| FORMULATION (F4) | |
| --- | --- |
| *Buchanania lanzan* linn | 10% |
| Sodium banzoate | 0.5% |
| Syrup containing sugar | Qs to make volume 100% |

Example-5

*Cissampelos pareira, Mangifera indica, Cinnamomum* sp. and *Buchanania lanzan* linn. were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. 15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16-mesh screen. Talc is added to the dried granules and then they are punched in the tablet-punching machine to form uniform tablets. Extracts were added in proper ratio to prepare the Syrup. The Syrup was prepared according to Indian Pharmacopoeia 1966. The formulation is useful for the treatment of various gastrointestinal disorders.

| FORMULATION (F5) | |
| --- | --- |
| *Cissampelos pareira* | 10% |
| *Mangifera indica* | 10% |
| *Cinnamomum* sps. | 10% |
| *Buchanania lanzan* linn | 10% |
| Sodium banzoate | 0.5% |
| Syrup containing sugar | Qs to make volume 100% |

Example-6

Evaluation of the Effect on Normal Defecation

Groups of six mice each were placed individually in separate cages with filter papers at the bottom. Different doses of the extracts were administered orally to different groups. The non-specific antidiarrhoeal reference drug diphenoxylate HCl (5.0 mg kg$^{-1}$, p.o.) and 1% CMC (10 mg kg$^{-1}$, p.o.) were administered to two groups and later served as controls (Melo et al, *J. Pharm. Pharmacol.* 40 (1988), 79–826). The total number of the faecal matter in each group was assessed every hour for the next 4 h. Percent reduction in the total number of faeces in the treated groups was obtained by comparison with control animals. The formulation F5 contains *Cissampelos pareira, Mangifera indica, Cinnamomum* sp. and *Buchanania lanzan* and the percentage reduction in causing diarrhea was reduced to 76.9% (Table 1) than that of the other combinations even than the standard allopathic drug. Table 1 reveals that F5 is highly synergistically effective.

TABLE 1

| Treatment | Dose (mg kg$^{-1}$) | Total no of faecal matter | % Reduction (Inhibition) |
| --- | --- | --- | --- |
| Control 1% CMC | — | 65 | — |
| F1 | 25 | 54 | 16.92 |
| F2 | 25 | 39 | 40.00 |
| F3 | 25 | 40 | 38.46 |
| F4 | 25 | 42 | 35.38 |
| F5 | 25 | 15 | 76.92 |
| Diphenoxylate HCl | 5.0 | 16 | 75.38 |

Values are presented of six rats in each group.

Note: There is no mortality/gross abnormality was observed in the animals during the treatment of without *C. pareira* containing formulation Example-7

Castor Oil-induced Diarrhoea

The method of Awouters et al. (J. Pharm. Pharmacol, 30, 1978, 41–45) as modified by Nwodo and Alumanah (J. Ethnopharmacol, 31, 1991, 395–398) was used. Briefly, rats fasted for 24 h were randomly allocated to five groups of six animals each. One group received 1% CMC (10 mL kg$^{-1}$, p.o.), other groups received orally the different dosage of drug extract. Another group given diphenoxylate HCl (5.0 mg kg$^{-1}$, p.o.) as suspension. After 60 min each animal was given with 2 ml of castor oil by orogastric cannula, and placed in a separate cage and observed for 4 h defecation. Transparent plastic dishes were placed beneath each cage and the characteristic diarrhoeal droppings were noted. The total number of the faecal matter in each group was assessed every hour for the next 4 h. Percent reduction in the total number of faeces in the treated groups was obtained by comparison with control animals. The formulation F5 contains *Cissampelos pareria, Mangifera indica, Cinnamomum* sp. and *Buchanania lanzan* and the percentage reduction in causing diarrhea was reduced to 76.9% (Table 1) than that of the other combinations even than the standard allopathic drug. Table 1 reveals that F5 is highly synergistically effective.

Example-8

Castor Oil-Induced Fluid Accumulation and Na$^+$ and K$^+$ Secretion

This was determined according to the method of Robert et al. (Prostaglandins 11, 1976, 809–814) modified by Di Carlo et al. (Phytother. Res. 8, 1994, 42–45). The rats fasted for 24 h but free access to water were randomized and allocated to different groups of six rats each. Group I (control) was administered 1% CMC (10 ml kg$^{-1}$, p.o.), group II was administered castor oil only (2 ml), and other groups were administered with different dosage of various formulations, 1 h prior to castor oil administration.

After 30 min the rats were killed by cervical dislocation and exsanguinated; the small intestine was ligated both at pyloric sphincter and at the ileocaecal junctions. The entire small intestine was dissected out, its contents were expelled into a graduated measuring cylinder and the volume of the contents was recorded and the fluid samples were analyzed for Na$^+$ and K$^+$ concentrations using flame photometer (Elico® CL361, India). The results are given in Table 2 which reveals that there is significant decrease in intestinal fluid at 50 and 100 mg/kg dose and the levels of $Na^+$ and $K^+$ was 151.6±09.6 to 105.4±06.9 and 6.2±0.28 to 5.6±0.31. It is a highly effective formulation as $Na^+$ and $K^+$ ions are maintained through out in treatment. The level of $K^+$ ion was only significant only at 100 mg/kg.

TABLE 2

| Treatment | Dose (mg Kg-1) | Intestinal fluid (ml) | Milliequivalent $L^{-1}$ | |
|---|---|---|---|---|
| | | | $Na^+$ | $K^+$ |
| Control 1% CMC | — | 0.98 ± 0.20 | 148.5 ± 16.5 | 5.1 ± 0.40 |
| Castor oil | 2 ml | 2.86 ± 0.35$^b$ | 190.7 ± 12.1 | 6.4 ± 0.71$^a$ |
| F5 | 25 | 2.14 ± 0.34 | 151.6 ± 09.6 | 6.2 ± 0.28 |
| F5 | 50 | 1.82 ± 0.17$^y$ | 136.1 ± 10.1$^x$ | 6.1 ± 0.37 |
| F5 | 100 | 1.12 ± 0.10$^z$ | 105.4 ± 06.9$^y$ | 5.6 ± 0.31$^x$ |

*Values are mean ± SEM for six rats.
P: $^a$<0.05 and $^b$<0.001 compared to respective control.
P: $^x$<0.05, $^y$<0.01 and $^z$<0.001 compared to respective castor oil group Example-9

Small Intestinal Transit

Animals were divided into four groups of six rats each and each animal was given orally 1 ml of charcoal meal (5% activated charcoal suspended in 1% CMC) 60 min after an oral dose of drugs or vehicle. Group I was administered with 1% CMC (10 ml $kg^{-1}$) and animals in the other groups received various formulations. Another group received atropine sulfate (0.1 mg $kg^{-1}$, IP) as standard drug. After 30 min animals were killed by cervical dislocation and the intestine was removed without stretching and placed lengthwise on moist filter paper. The length of the intestine (pyloric sphincter to caecum) and the distance travelled by the charcoal as a percentage of that length were evaluated for each animal, and group means were compared and expressed as percentage inhibition (Lutterodt, J. Ethnopharmacol. 25, 1989, 235–247). It is evident from Table 3 that the percentage reduction of F5 formulation on castor oil stimulated gastrointestinal transit is 43.19–66.70% and the distance travelled by charcoal was 27.6±3.2 to 50.9±2.6 with the dose of the formulations. Therefore the dose dependent effect of the formulation was similar to the synthetic drug atropine. But long use of atropine completely blocks the secretions it is an adverse effect.

TABLE 3

| Treatment | Dose (mg $kg^{-1}$) | Mean intestinal length (cm) | Mean distance travelled by charcoal (cm) | Reduction (%) |
|---|---|---|---|---|
| Control (1%, 10 ml $kg^{-1}$CMC) + Charcoal meal | — | 84.6 ± 4.3 | 62.5 ± 5.1 | 26.12 |
| F5 + Charcoal meal | 25 | 89.6 ± 2.7 | 50.9 ± 2.6$^a$ | 43.19 |
| F5 + Charcoal meal | 50 | 87.6 ± 3.9 | 36.1 ± 1.8$^a$ | 58.79 |
| F5 + Charcoal meal | 100 | 82.9 ± 1.8 | 27.6 ± 3.2$^b$ | 66.70 |
| Atropine sulphate + Charcoal meal | 0.1 | 83.7 ± 5.2 | 26.5 ± 2.6$^b$ | 68.33 |

*Values are mean ± SEM for six rats.
P: $^a$<0.01 and $^b$<0.001 compared to control (1%, 10 ml $kg^{-1}$CMC) + charcoal meal Note: There is no mortality/gross abnormality was observed in the animals during the treatment of *C. pareira* containing formulation.

Example-10

Protection Against Acute Gastric/Duodenal Ulcers

To assess the efficacy of different formulations against the indomethacin induced gastric ulcer different doses (25–100 mg $kg^{-1}$, p.o.) of formulations were administered to groups of 10 mice for each dose, while one group of the same number of mice served as control and the results are given in Table 4. The results of Table 4 represents that there is a significant and dose dependent anti ulcer activity and percentage ratio ranges of protection from 27.03 to 75.38. The pH of the formulation F5 is neutral while the stomach pH before treatment was 2.5–4.2, while after treatment the pH was found to be towards alkaline (>7). The synthetic/allopathic drug ranitidine showed 82.20% which is almost similar to that of formulation F5 but long use block the normal secretions in the stomach.

Table 5 shows the efficacy of the formulation F5 against duodenum ulcer. The efficacy is compared with the known standard synthetic drug Ranitidine for treatment of. It is evident from table 5 that the formulation F5 shows protection of 90.2% where as the same is 77% in case of standard synthetic drug as. Where as the formulation F5 contains *C. pareira*, *M. indica*, *Cinamommum* sp. and *Buchanania lanzan*.

TABLE 4

| Treatment | Dose (mg/kg) | Ulcer index | % Curative ratio |
|---|---|---|---|
| Control (1% CMC) | — | 4.55 ± 0.50 | — |
| Formulation F5 | 25 | 3.32 ± 0.22 | 27.03 |
| Formulation F5 | 50 | 2.41 ± 0.02$^a$ | 47.03 |
| Formulation F5 | 100 | 1.12 ± 0.01$^b$ | 75.38 |
| Ranitidine | 50 | 0.81 ± 0.01$^b$ | 82.20 |

Values are mean ± SEM for six rats.
P: $^a$<0.01 and $^b$<0.001 compared to control group

TABLE 5

| Treatment | Dose (mg/kg) | Ulcer incidence | | Ulcer score | % Protection |
|---|---|---|---|---|---|
| | | No | % | Total lesion area (mm$^2$) | |
| Control (1% CMC) | — | 8/10 | 80 | 4.80 ± 0.37 | — |
| Formulation 5 | 25 | 6/10 | 60 | 2.80 ± 0.24 | 41.7 |
| Formulation 5 | 50 | 4/10 | 40 | 1.51 ± 0.31$^a$ | 68.5 |
| Formulation 5 | 100 | 2/10 | 20 | 0.47 ± 0.10$^b$ | 90.2 |
| Ranitidine | 50 | 2/10 | 20 | 1.06 ± 0.17$^c$ | 77.9 |

Values are mean ± SEM for ten rats.
P: $^a$<0.05, $^b$<0.01 and $^c$<0.001 compared to respective control group Example-11

Estimation of Free Radical Generation

The mucosal scrapping of the small intestine was homogenized (5%) in ice-cold 0.9% NaCl with a Potter-Elvehjem glass homogenizer for 30 seconds. The homogenate was centrifuged at 800×g for 10 min followed by centrifugation of the supernatant at 12,000×g for 15 min to get the mitochondrial fraction used for the following estimations (Das and Banerjee, Mol. Cell Biochem. 125, 1993, 115–125). The levels of lipid peroxidase (LPO) (Ohkawa et al, Anal. Biochem. 95, 1979, 351–358) along with the activities of enzymes such as superoxide dismutase (SOD) (Kakkar et al, Indian J. Biochem. Biophys. 21, 1984, 130–132) and catalase (CAT) (Aebi, Catalase, in Methods in Enzymatic Analysis, 2 Ed, (Ed.: H. U. Bergmeyer) Acadamie Press, New York 1952, Vol. 3, pp. 673) were estimated.

Example-12

General Gross Behaviour and Acute Toxicity Studies

Different doses (25–2000 mg kg$^{-1}$, p.o.) of formulations were administered to groups of 10 mice for each dose, while one group of the same number of mice served as control. The animals were observed continuously for 1 h and then at half-hourly intervals for 4 h, for any gross behavior changes, including general motor activity, writhing, convulsions, response to tail pinching, gnawing, piloerection, pupil size, fecal output and feeding behavior and further up to 72 h for any mortality. Acute LD$_{50}$ (50% lethal dose) value in mice were calculated by the method of Miller and Tainter (Proc. Soc. Exp. Biol. Med. 57, 1944, 261–264).

| References Cited | | |
|---|---|---|
| 20030119916 | Jun. 26, 2003 | Fowler, David |
| 6,187,313 | February, 2001 | Segelman |
| 5,728,384 | March, 1998 | Tokuyama |

Sairam et al. J. Ethnopharmacology. 82 pp. 1–9, 2002.
Narayanan et al. J. Ethnopharmacology. 65, 237–241, 1999.
Sairam et al. Phytomedicine, 86 (6), pp. 423–430, 2001.
Sairam et al. Indian J. Exp. Biol. 39, 350–354, 2001.
Rao et al. Indian J. Physiol. Pharmacol, 44(4), pp. 435–441, 2000.
Rao et al. Acta Pharmaceutica Turcica, 45, 85–91, 2003.
Remington, The science and practice of pharmacy, 19th edition, Vol II. pp. 1635, 1995 Jain S K. Dictionary Of Indian Folk Medicine And Ethnobotany, Deep publications, New Delhi. pp. 221, 1991.
Chopra R N, Nayar S L and Chopra I C. *Glossary of Indian Medicinal Plants*, CSIR, New Delhi, 8, 1958.
Anonymous, *Indian Medicnal Plants*, Vol. 2, Orient Longman Ltd. publication, Madras. 84–86, 1994

We claim:

1. A herbal composition to treat gastro-intestinal disorders, said composition comprising 5 to 10% by wt. of extract from *Mangifera indica*, 5 to 10% by wt. of *Cissampelos pareira*, 5 to 10% by wt. of *Cinnamomum* sp., and 5 to 10% by wt. of *Buchanania lanzan* optionally along with other pharmacologically acceptable binders, diluents and lubricants.

2. A herbal composition as claimed in claim 1, wherein the gastro-intestinal disorder is diarrhea, dysentery, gastric ulcer, duodenal ulcer, stomach ache, irritable bowel syndrome or a spasmodic disorder.

3. A herbal composition as claimed in claim 1, wherein the said composition is synergistic mixture of plant extracts having antioxidant, hepatoprotective, digestive, choleretic, nervine relaxant and immuno-enhancing properties.

4. A herbal composition as claimed in claim 1, wherein the plant extracts are obtained from plant parts selected from root, seed and aerial parts.

5. A herbal composition as claimed in claim 1, wherein the extract of *Cissampelos pareira* is obtained from root.

6. A herbal composition as claimed in claim 1, wherein the extract of *Mangifera indica* is obtained from seed kernel.

7. A herbal composition as claimed in claim 1, wherein the extract of *Cinnamomum* sp. is obtained from leaves and bark.

8. A herbal composition as claimed in claim 1, wherein the extract of *Buchanania lanzan* is obtained from bark.

9. A herbal formulation as claimed in claim 1 wherein the extracts of plants are 50% aqueous alcoholic extracts.

10. A herbal composition as claimed in claim 1 wherein the said binder is starch, starch paste, gum acacia or carboxy methyl cellulose.

11. A herbal composition as claimed in claim 1 wherein the diluent used is lactose.

12. A herbal composition as claimed in claim 1 wherein the lubricant is starch or lactose.

13. A herbal composition as claimed in claim 1 wherein a sugar syrup is used as a vehicle.

14. The herbal composition as claimed in claim 13 wherein the sugar syrup used as a vehicle is about 67% w/w sugar.

15. A herbal composition as claimed in claim 1, wherein the said composition comprises about 15–50% wt of the total formulation.

16. A method of preparing a herbal composition, said method comprising:
   a. obtaining one or more parts of *Mangifera indica*, *Cissampelos pareira*, and *Cinnamomum* sp medicinal plants, and optionally one or more parts of *Buchanania lanzan*, wherein said parts comprise leaves, bark, root seed, seed kernel or aerial parts;
   b. drying the one or more plant parts of step (a);
   c. forming the dried plant material of step (b) into powdered dried plant material;
   d. extracting the powdered dried plant material of step (c) with an aqueous alcohol at a temperature in the range of 25 to 35° C. to provide an aciueous alcohol extract;
   e. concentrating the extract obtained in step (d) under reduced pressure;
   f. obtaining a dried extract by lyophilising the concentrated extract for complete removal of solvent; and
   g. mixing the extract of *Mangifera indica, Cissampelos pareira*, and *Cinnamomum* sp, and optionally the extract of *Buchanania lanzan* if obtained in step (a), with other pharmacologically acceptable binders, diluents or lubricants to prepare the composition.

17. A process of preparation of herbal composition as claimed in claim 16, wherein the medicinal plants of step (a) comprise *Mangifera indica, Cissampelos pareira, Buchanania lanzan* and *Cinnamomum* sp.

18. A process as claimed in claim 16, wherein in step (d) the extraction is carried out by using 40–50% aqueous ethanol.

19. A process of preparation of herbal composition as claimed in claim 16, wherein the plant extracts are obtained: from plant *Mangifera indica, Cissampelos pareira*, and *Cinnamomum* and the plant parts are selected from root, seed and aerial parts.

20. A process of preparation of herbal composition as claimed in claim 16, wherein the extract of *Cissampelos pareira* is from a root.

21. A process of preparation of herbal composition as claimed in claim 16, wherein the extract of *Mangifera indica* is from a seed kernel.

22. A process of preparation of herbal composition as claimed in claim 16, wherein the extract of *Cinnamomum* sp. is from leaves.

23. A process of preparation of herbal composition as claimed in claim 16, wherein the extracts of plants obtained in step (d) are 50% aqueous alcoholic extracts.

24. A process of preparation of herbal composition as claimed in claim 16, wherein in step (g) the said binder is starch, starch paste, gum acacia or carboxy methyl cellulose.

25. A process of preparation of herbal composition as claimed in claim 16, wherein in step (g) the diluent used is lactose.

26. A process of preparation of herbal composition as claimed in claim 16, wherein in step (g) the lubricant is starch or lactose.

27. A process of preparation of herbal compositions as claimed in claim 16, wherein the said composition comprises about 25–50% wt of the total formulation.

28. The process as claimed in claim 16, wherein in step (d) the extraction is carried out using an aqueous alcohol in a ratio of 1:8 to 1:15 for about 4–7 days.

29. The process as claimed in claim 16, wherein in step (e) the concentrating under reduced pressure is carried out at a temperature in the range of about 40–60° C.

30. The process as claimed in claim 16, wherein the composition comprises about 5–15% by wt. of each of *Mangifera indica, Cissampelos pareira, Buchanania lanzan* and *Cinnamomum* sp. dried extracts.

31. A method of treatment of gastro-intestinal disorder by administering a pharmaceutically acceptable amount of a composition comprising extracts from *Mangifera indica, Cissampelos pareira, Cinnamomum* sp, and *Buchanania lanzan* to a subject in need thereof.

32. A method of treatment as claimed in claim 31, wherein the subject is a mammal.

33. A method of treatment as claimed in claim 31, wherein said composition is applied as an oral dosage and said oral dosage is in the form of a syrup, tablet, capsule or powder.

34. A method of treatment as claimed in claim 33, wherein the dosage is 25 to 100 mg/kg.

35. A method of treatment as claimed in claim 33, wherein the dosage is 25 to 100 mg/kg in castor oil induced fluid accumulation, wherein the concentration of sodium in the accumulated fluid is reduced to 151.6±9.6 to 105.4±06.9 milliequivalents per liter, as determined by flame photometry.

36. A method of treatment as claimed in claim 33, wherein the dosage is 25 to 100 mg/kg in castor oil induced fluid accumulation, wherein the concentration of potassium in the accumulated fluid is reduced to 6.4±0.71 to 5.6±0.31 milliequivalents per liter, as determined by flame photometry.

37. A method of treatment as claimed in claim 31, wherein the composition immediately relieves the acidity of the stomach by neutralizing the excess acid.

* * * * *